US00PP11295P

United States Patent [19]

Moon

[11] Patent Number: Plant 11,295

[45] Date of Patent: Mar. 21, 2000

[54] LACEBARK ELM TREE NAMED 'UPMTF'

[75] Inventor: Dwayne C. Moon, Loganville, Ga.

[73] Assignee: Tree Introductions, Inc., Bishop, Ga.

[21] Appl. No.: 09/020,069

[22] Filed: Feb. 6, 1998

[51] Int. Cl.[7] ..... A01H 5/00

[52] U.S. Cl. ..... Plt./221

[58] Field of Search ..... Plt./221

*Primary Examiner*—Howard J. Locker

*Attorney, Agent, or Firm*—Klarquist Sparkman Campbell Leigh & Whinston, LLP

[57] ABSTRACT

A lacebark elm tree named 'UPMTF' having an upright pyramidal growth habit with a dense foliage canopy, a dominant leader with secondary branches ascending upwardly, early exfoliating bark, consistent rich yellow-orange fall color, and also capable of being reproduced reliably from vegetative cuttings.

6 Drawing Sheets

DESCRIPTION

The present invention relates to a new and distinct variety of *Ulmus parvifolia*, Lacebark Elm, which has been given the varietal name 'UPMTF'.

I discovered the original tree of my new variety as a chance seedling growing in 1993 in a production field in a cultivated area at Moon Tree Farm in Loganville, Ga. This initial tree of my new variety originated as a seedling, was grown for two years in a liner row, and was then transplanted into the field. It is now nine years old. As I observed the original tree of my new variety, the uniqueness of this tree became apparent because of its dominant leader and upright growing form.

I observed this initial tree of my new variety for a period of time and believe it is particularly useful in landscape settings where structurally sound, upright tree forms are important, such as along streets, buildings, and in parking areas.

In contrast, cultivated lacebark elm trees are still somewhat represented by seedling material that is extremely variable in growth habit, and several other varieties ranging form oval to vase-shaped to broad-rounded. The single dominant leader trait of my new variety has not been observed by me in any lacebark elm seedling or cultivar.

Lacebark elm typically is a large tree that matures between forty to fifty feet high and wide, is adaptable to soil and climate, and has a native range from southern China in a broad arc over to Korea and into northern Japan. Its United States adaptability, based on observed successful culture, ranges from Massachusetts to central Florida to Iowa, south to Texas and west to Washington State and California. There is a need for adaptable and tolerant trees that can be grown over a wide geographic area. Consequently, a new variety of lacebark elm which has a narrow, pyramidal habit and displays clonal consistency is particularly useful.

My new variety has been asexually propagated in Georgia from softwood cuttings at my direction.

This propagation and observation of the resulting progeny have proven the characteristics of my new variety of lacebark elm to be firmly fixed. Furthermore, these observations have confirmed that my new variety represents a new and improved variety of lacebark elm as particularly evidenced by the unique narrow, pyramidal growth habit and which can reliably be asexually propagated using vegetative propagation techniques.

The accompanying photographs depict the color of the tree and foliage of my new variety as nearly true as is reasonably possible to make the same in a color illustration of this character.

My 'UPMTF' variety of lacebark elm has not been observed under all growing conditions and thus variations may occur as a result of different growing conditions. The following is a detailed description of my new variety of lacebark elm with color terminology in accordance with The Royal Horticultural Society color chart (R.H.S.) published by The Royal Horticultural Society of London. The observations are of the original tree of my new variety growing at the Moon Tree Farm site in Loganville, Ga.

My new variety of lacebark elm is characterized by its central dominant leader and pyramidal habit. In 1992, the initially discovered tree of my new variety was four years old and was transplanted form a liner row to a production field at the Moon Tree Farm site in Loganville, Ga. It was then discovered in 1993. In December of 1995, the original tree was eighteen feet high and eight feet wide with four inches of caliper six inches above the ground with a height to width ratio of 2.25. This upright pyramidal form with a dominant leader distinguishes my new variety from typical *Ulmus parvifolia* trees. Most lacebark elms are round-headed, often with pendulous branches, with some forms being upright-spreading.

My new tree maintains a dominant leader with strongly ascending secondary branches forming an upright pyramidal outline. In contrast, seedlings and other cultivars which I have observed do not have a dominant leader. The unique growth habit insures its capacity for use in areas where growing space is restricted, particularly along streets with buildings or sites which will not accommodate a broader canopy.

Figure 1:
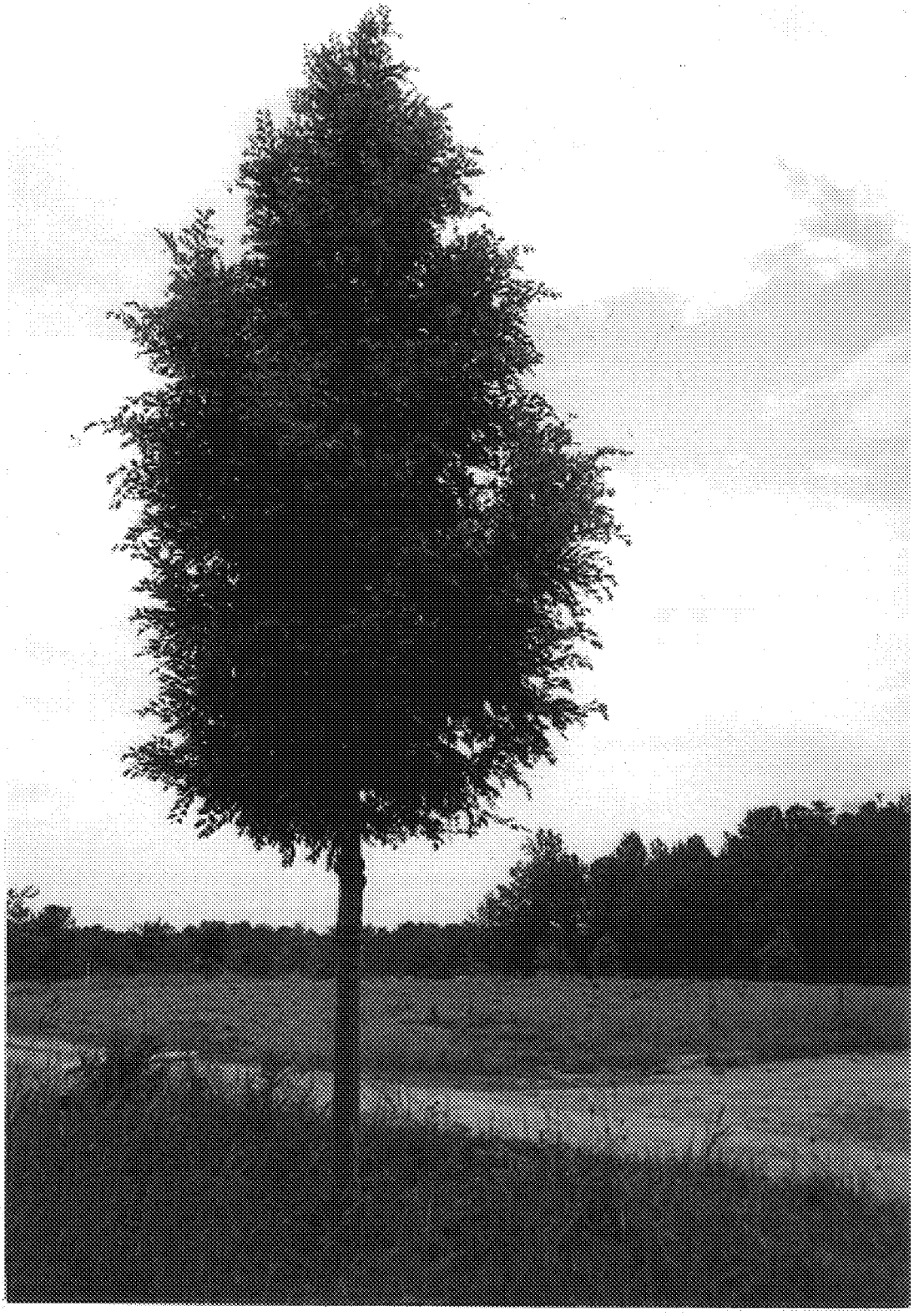
FIG. 1 is a photograph of an entire tree of my new variety.
Figure 2:
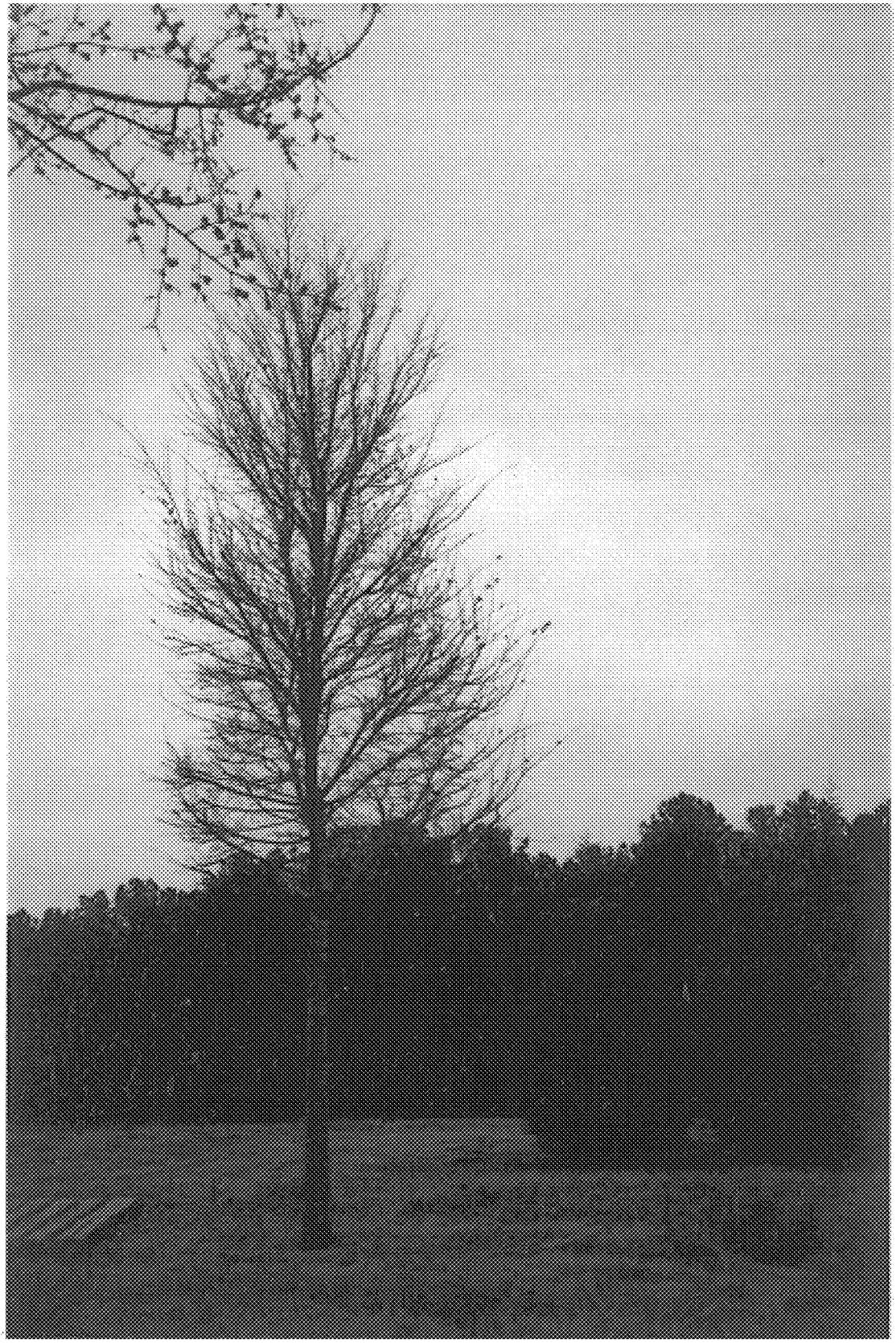
FIG. 2 is a photograph of an entire tree of my new variety showing winter habit and branch structure.

More specifically, my new tree has a branching habit and dendritic pattern of a dominant single lead (bole) with secondary branches that emerge at sixty degree angles (base)

and thirty degree angles (top) to the main leader. Branches are uniformly and densely borne around the central leader with no large gaps from one branch insertion to the next. As a result, as can be seen from FIG. 2, the tree of my new variety is uniformly branched and symmetrical with a dense canopy. In contrast, traditional seedling lacebark elms and some of the cultivars are usually open and in youth must be pruned often to produce an upright habit.

Figure 3:
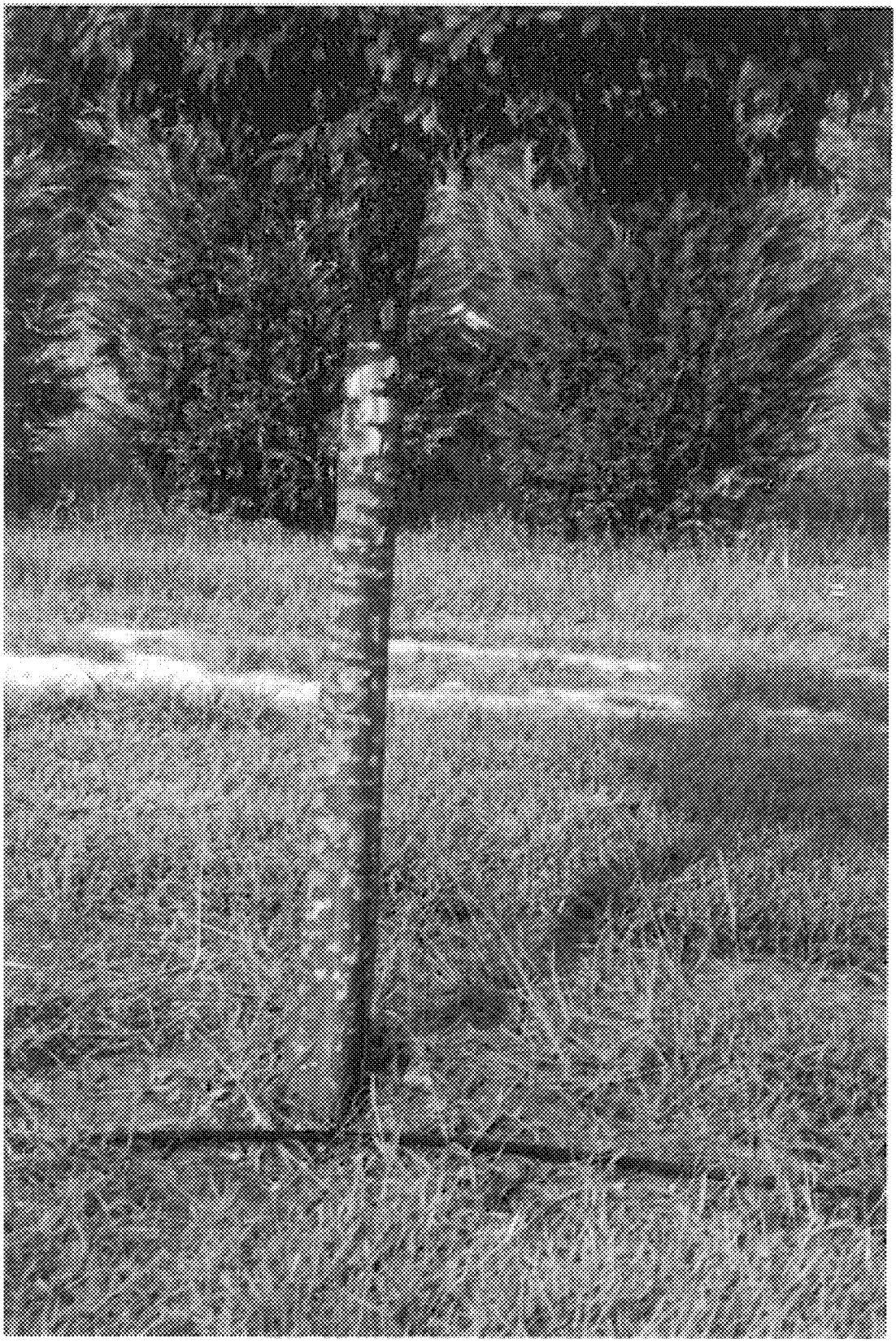
FIG. 3 is a close up of a trunk of my new variety showing mature bark.
Figure 4:
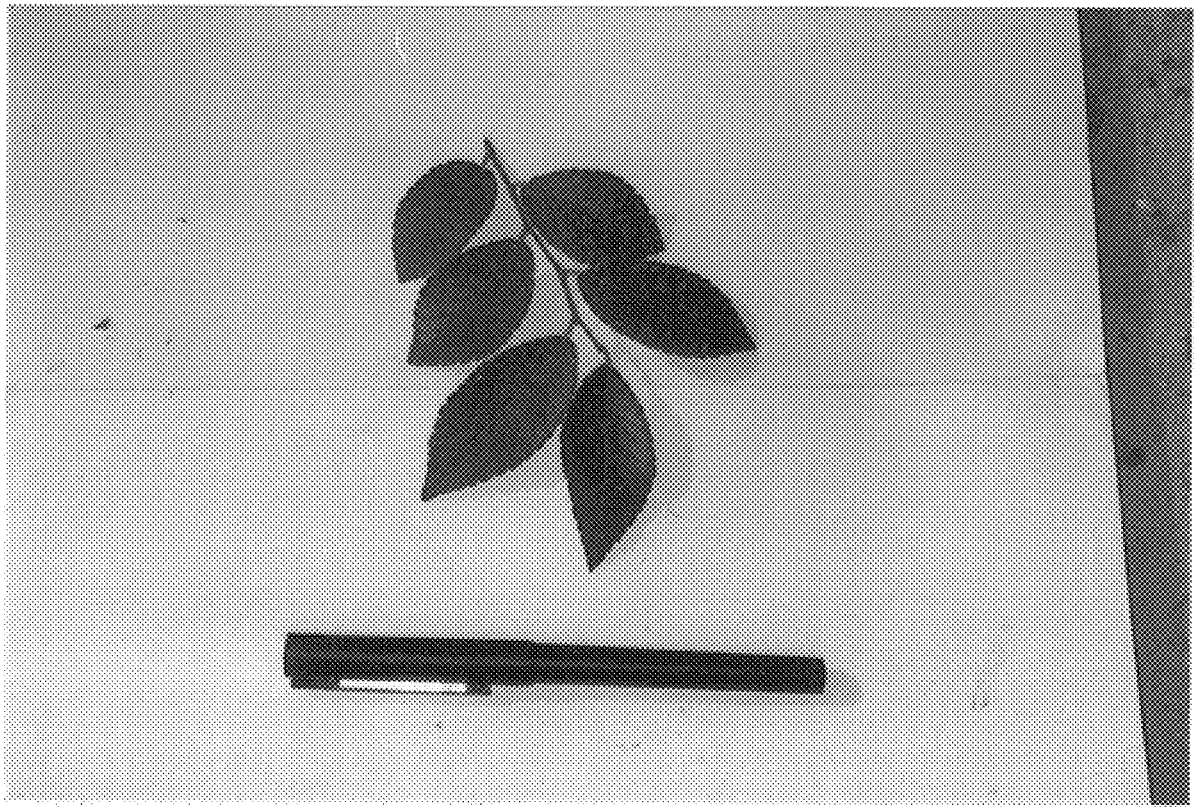
FIG. 4 is a close up of the upper surface of several leaves from a tree of my new variety.
Figure 5:
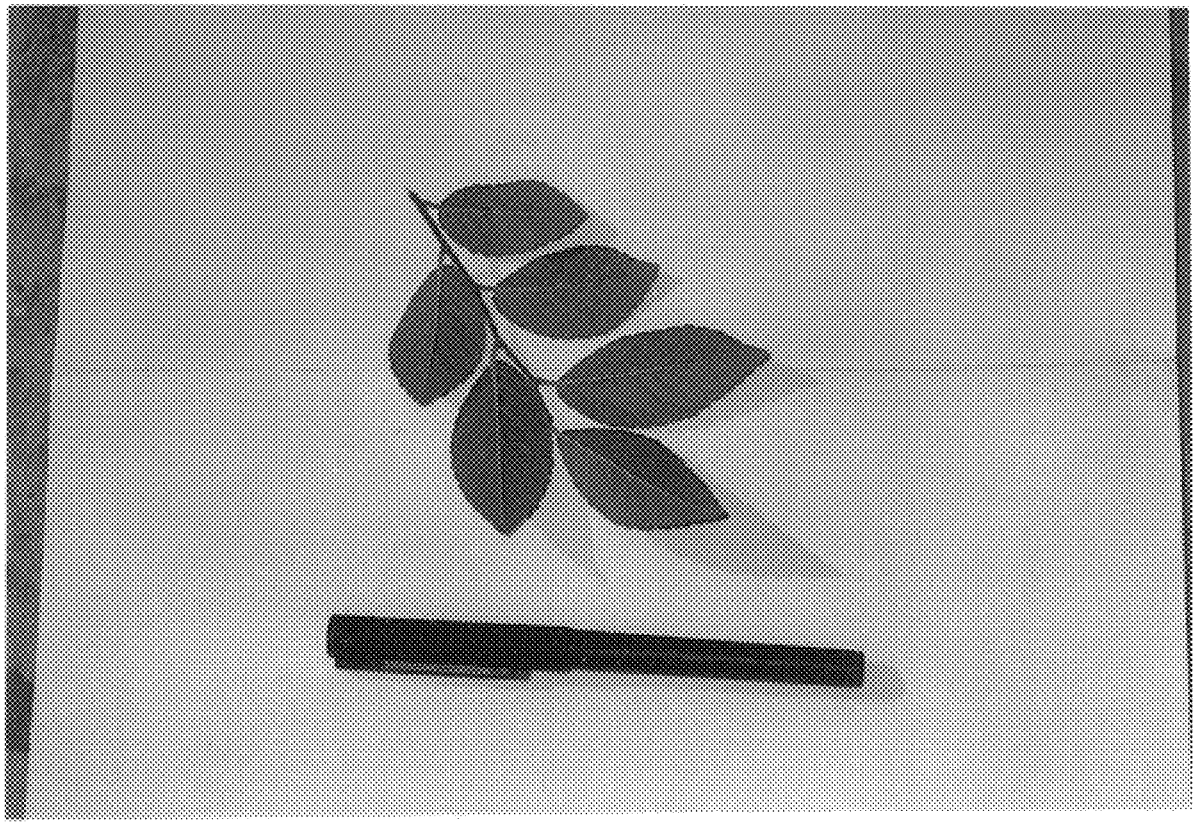
FIG. 5 is a close up of the lower surface of a several leaves from a tree of my new variety.
Figure 6:
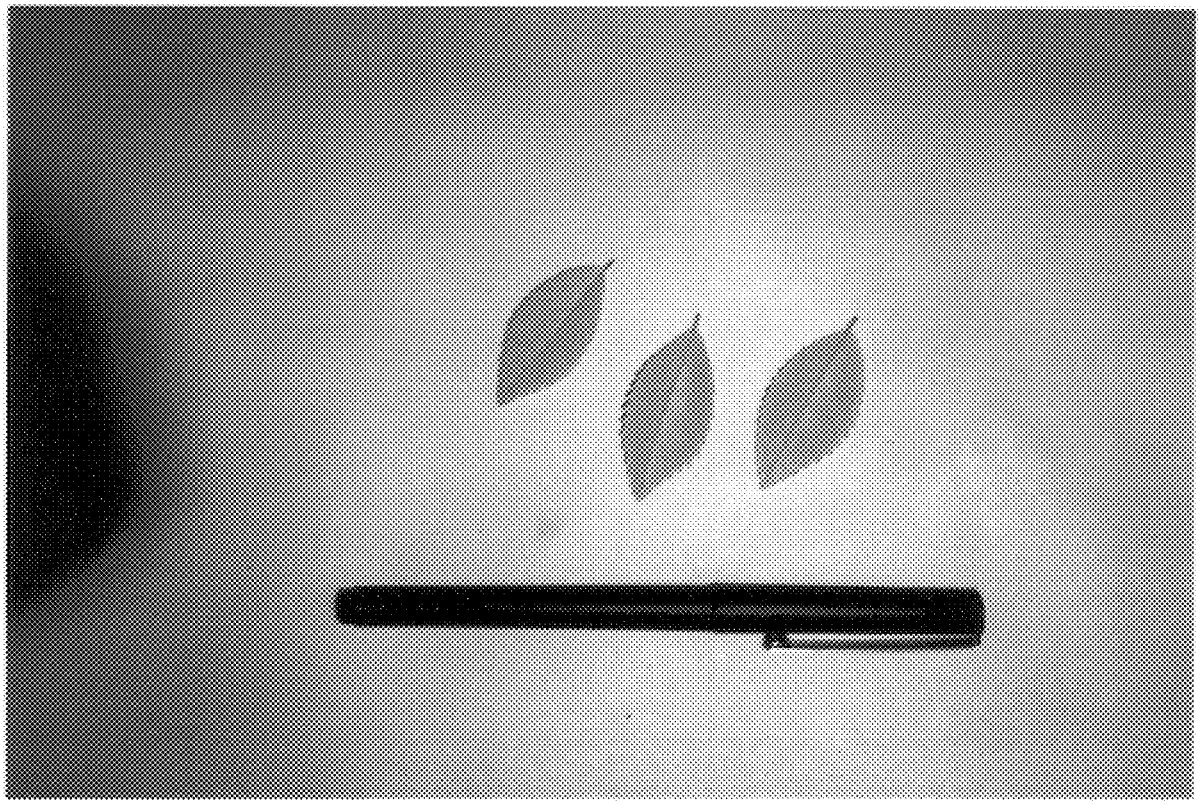
FIG. 6 is a close up of the upper surface of a number of leaves from a tree of my new variety showing the fall color.

The lower trunk and larger branches exfoliate at three inch caliper or larger. This is a desirable and unique characteristic of the variety, not typical of most seedling plants and found to varying degrees in the cultivars. The gray-orange and gray-brown coloration (R.H.S. 164B and R.H.S. 177B) is evident in FIG. 3.

The summer leaves are similar to those of the species, being dark green above, lighter below. In fall, the leaves turn yellow-orange. The upper leaf surface is lustrous dark green (R.H.S. 133A). The lower leaf surface is flat green (R.H.S. 135A). In fall, the leaves turn yellow-orange (R.H.S. 21A) and rival those of paper birch. The mature leaf averages three-fourths to two and one-half inches long, one-third to one and one-third inches wide, ten to twelve vein pairs, with one-fourth to one-half inch long petioles and is elliptical, as is typical of the species. Leaves are essentially glabrous at maturity.

Flowers and fruits have been observed only in the original tree and are typical for the species. My new tree initiated flowers in its fifth growing season.

THE PLANT

Parentage: Chance lacebark elm seedling of unknown origin, growing in a cultivated area of the Moon Tree Farm in Loganville, Ga.

Tree shape and growth: Upright-pyramidal. The growth rate is characterized as being very vigorous. Progeny of the original tree growing in USDA Zone 7a in Loganville, Ga., on average grew 1¼ inch caliper during the 1998 growing season. In computing this average, measurements were taken from 125 trees.

Trunk: Dominant leader, exfoliating with maturity.

Bark: Rich brown. Exfoliating on three inch caliper and larger trunk.

Mature bark color: (Observed in the original tree) Exfoliating on three inch caliper and larger branches to reveal patches of gray-orange and gray-brown coloration (R.H.S. 164B and R.H.S. 177B). The texture of the bark prior to exfoliation is somewhat smooth. The color prior to exfoliation is a gray brown (R.H.S. 199A.

Branches: Ascending, emerging from the dominant leader at an angle of sixty degrees (base) and thirty degrees (top).

Leaves: Leaf shape is elliptical and typical of the species.

Leaf surface: Upper leaf surface is lustrous dark green (R.H.S. 133A) and glabrous. The lower surface is flat green (R.H.S. 135A) and glabrous.

Leaf size: Leaves average three-fourths to two and one-half inches long, one third to one and one-third inches wide, ten to twelve vein pairs, with one-fourth to one-half inch long petioles.

Buds, flowers, and fruit: Observed in the original tree to be like those of the species. Flowers are inconspicuous and typically occur early in September in Georgia where the original tree is growing. The fruit is an elliptic-ovate samara, one-third of an inch long and glabrous.

Disease resistance: The original tree seems to be fairly disease resistant and has not shown any signs of significant heat scorch or dieback. While the tree has not been inoculation tested for resistance to Dutch Elm Disease, the species is not known to be affected.

Winter hardiness: The original tree withstood 4 degrees F. without injury and laboratory tests have showed it to be hardy to −16 degrees F. It is expected to be hardy to USDA Zone 6, but has not been tested outdoors yet in those areas.

I claim:

1. A new and distinct variety of lacebark elm tree substantially as herein shown and described, characterized particularly as to novelty by its unique upright pyramidal growth habit, thirty to sixty degree ascending branch angles, early developing and spectacular bark, and yellow-orange fall color.

* * * * *